United States Patent [19]

Hall et al.

[11] Patent Number: 4,474,803
[45] Date of Patent: Oct. 2, 1984

[54] 7-OXABICYCLOHEPTANE SUBSTITUTED THIO PROSTAGLANDIN ANALOGS USEFUL IN TREATING PLATELET AGGREGATION AND BRONCHOCONSTRICTION

[75] Inventors: Steven E. Hall, Ewing Township, Mercer County; Martin F. Haslanger, Lambertville, both of N.J.

[73] Assignee: E. R. Squibb & Sons, Inc., Princeton, N.J.

[21] Appl. No.: 474,913

[22] Filed: Mar. 14, 1983

[51] Int. Cl.³ ............... C07D 307/00; A61K 31/34; A61K 31/557
[52] U.S. Cl. .................................. 424/285; 549/463
[58] Field of Search .................. 549/463; 424/285

[56] References Cited

U.S. PATENT DOCUMENTS

| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0032292 6/1982 European Pat. Off. .
2039909 8/1980 United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted thio prostaglandin analogs are provided having the structural formula

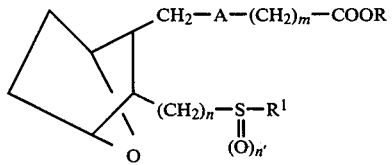

wherein R is hydrogen, lower alkyl or alkali metal, $R^1$ is lower alkyl, arylalkyl, aryl, cycloalkyl or cycloalkylalkyl. A is $-CH=CH$ or $-(CH_2)_2$, n is 1 to 4, n' is 0 to 2 and m is 1 to 8, and including all stereoisomers thereof.

The compounds are cardiovascular agents useful, for example, in the treatment of thrombolytic disease.

22 Claims, No Drawings

7-OXABICYCLOHEPTANE SUBSTITUTED THIO PROSTAGLANDIN ANALOGS USEFUL IN TREATING PLATELET AGGREGATION AND BRONCHOCONSTRICTION

DESCRIPTION OF THE INVENTION

The present invention relates to 7-oxabicycloheptane thio prostaglandin analogs which are cardiovascular agents useful, for example, in the treatment of thrombolytic disease. These compounds have the structural formula

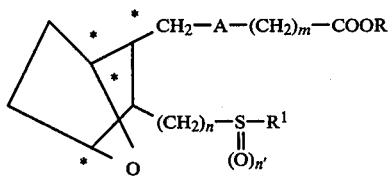

and including all stereoisomers thereof, wherein

A is CH=CH or $(CH_2)_2$, m is 1 to 8, n is 1 to 4, n' is 0, 1 or 2, R is H, lower alkyl or alkali metal, and $R^1$ may be lower alkyl, aryl, aralkyl, cycloalkyl or cycloalkylalkyl.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halosubstituent, such as F, Br, Cl or I or $CF_3$, an alkoxy substituent, a haloaryl substituent, a cycloalkyl substituent (that is, cycloalkylalkyl) or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The terms "$(CH_2)_m$" and "$(CH_2)_n$" includes a straight or branched chain radical having from 1 to 8 carbons in the normal chain in the case of "$(CH_2)_m$" and 1 to 4 carbons in the normal chain in the case of "$(CH_2)_n$" and may contain one or more lower alkyl substituents. Examples of $(CH_2)_m$ and $(CH_2)_n$ groups include $CH_2$, $CH_2CH_2$, $(CH_2)_3$, $(CH_2)_4$, $(CH_2)_5$, $(CH_2)_6$, $(CH_2)_7$,

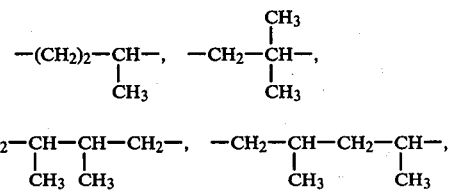

and the like.

Preferred are those compounds of formula I wherein A is $(CH_2)_2$ or CH=CH, m is 2 to 4, R is H, n is 0, 1 or 2, $R^1$ is pentyl, hexyl, cyclohexyl, cyclohexylmethyl, phenyl, benzyl, 2-phenylethyl or 3-phenylpropyl.

The various compounds of the invention may be prepared as outlined below.

A. Where n = 1

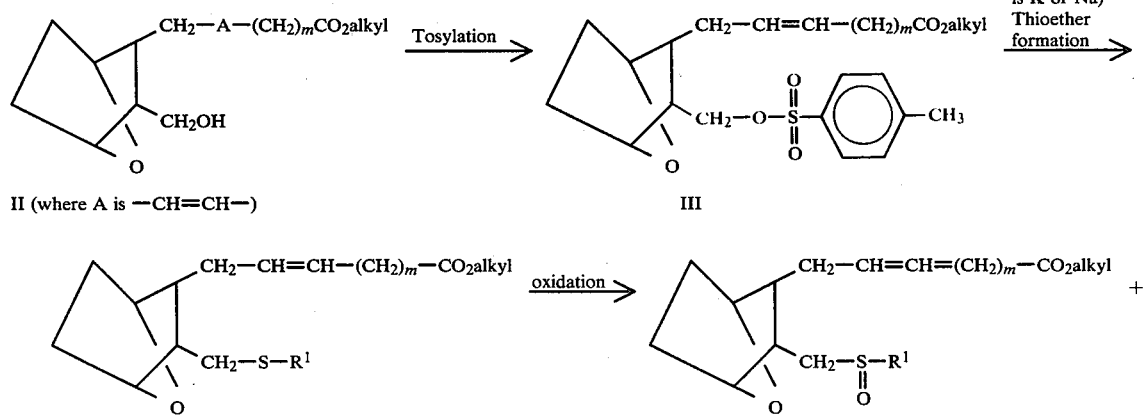

-continued
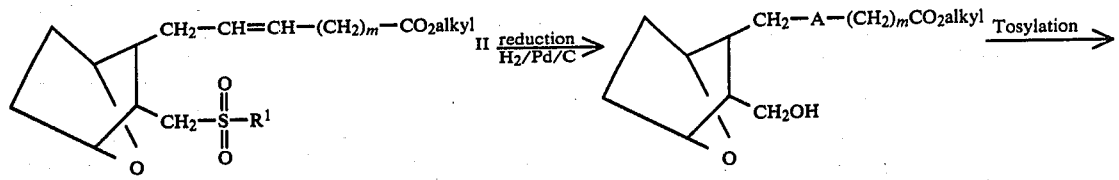
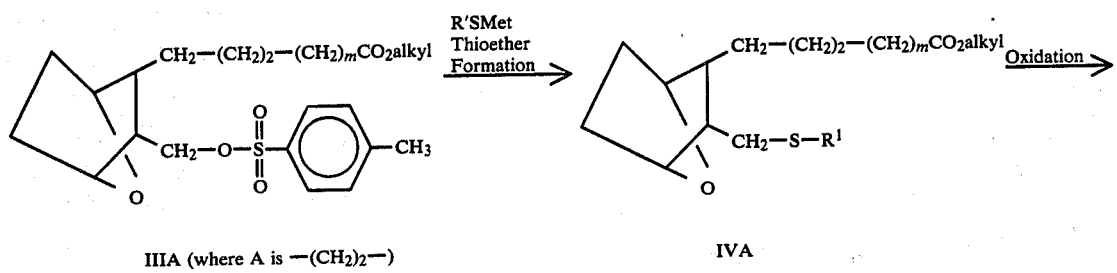
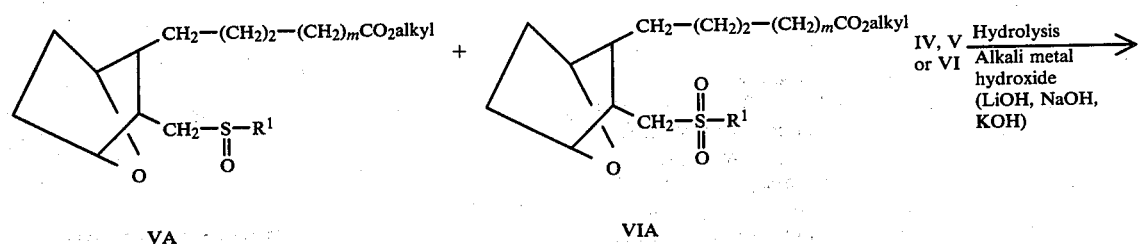
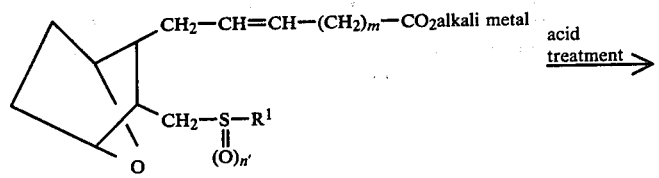
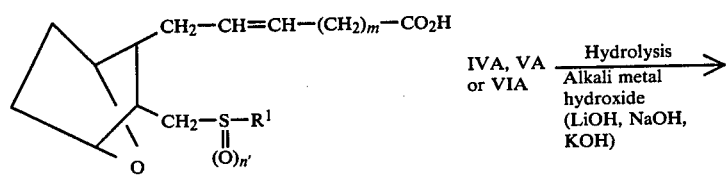
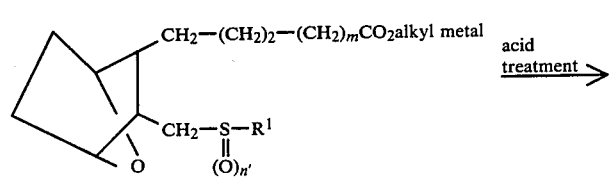

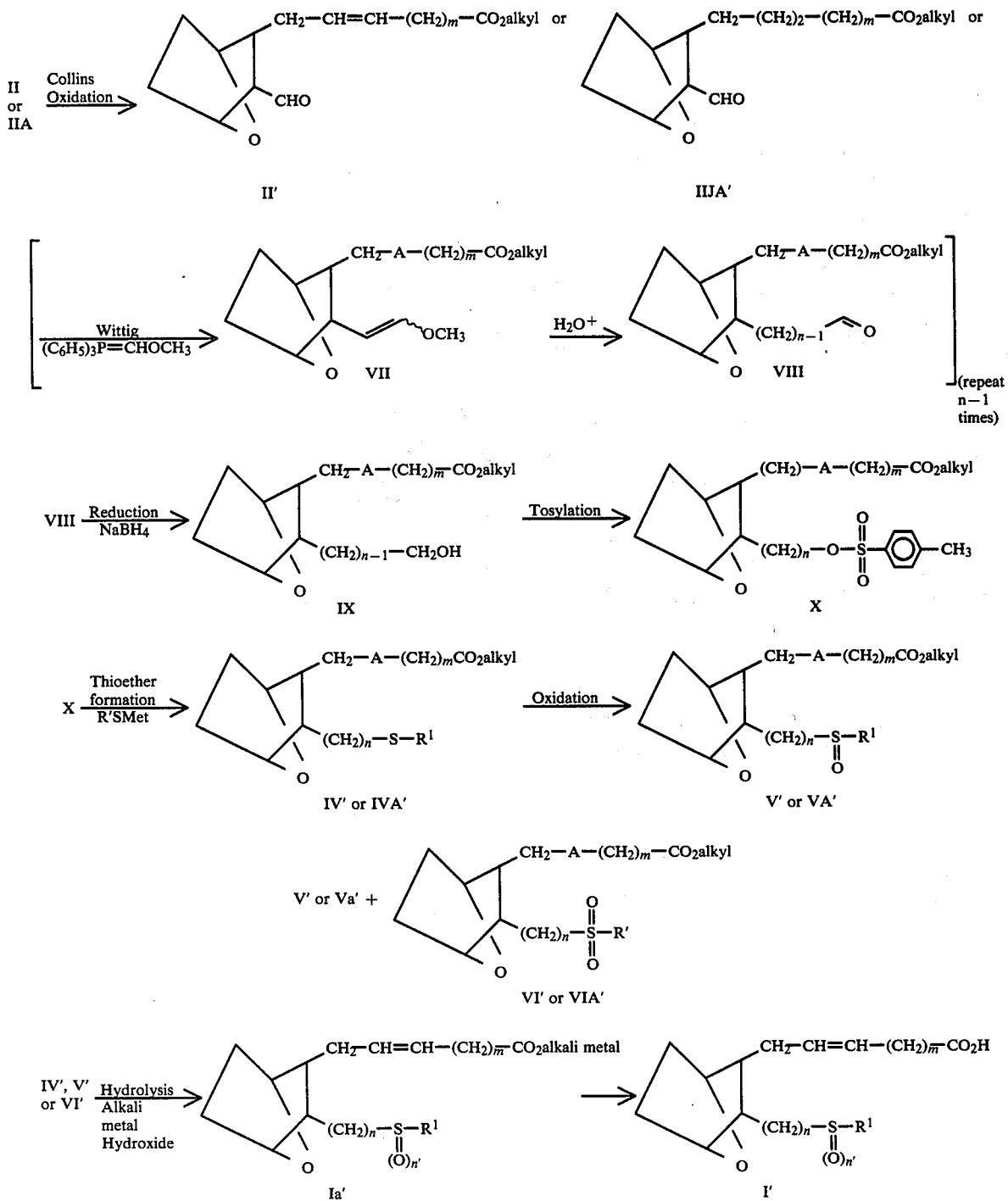

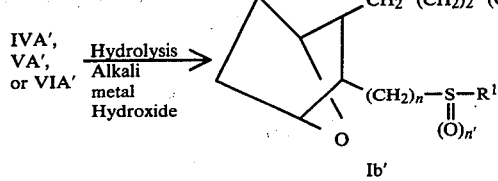

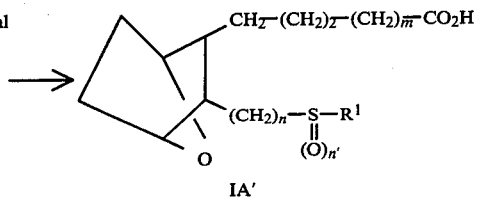

In the reaction sequence identified as "A", where the Formula I n is 1, the lower alkyl ester containing the hydroxymethyl group, that is, compound II (where A is —CH=CH—) or IIA (where A is —(CH$_2$)$_2$) (prepared as described in U.S. Pat. No. 4,143,054) is employed as the starting material. Thus, where A is —CH=CH—, compound II is subjected to a tosylation reaction, for example, by reacting II with tosyl chloride in pyridine to form tosylate III. To form the tosylate IIIA (where A is (CH$_2$)$_2$), compound II is reduced, for example with hydrogen over a palladium on carbon catalyst, to form hydroxymethyl compound IIA (where A is (CH$_2$)$_2$) and compound IIA is subjected to a tosylation reaction to form tosylate IIIA (where A is (CH$_2$)$_2$). Thereafter, tosylate III or IIIA is reacted with a thiol of the structure

R$^1$SH    A employing a molar ratio of III or IIIA:thiol of within the range of from about 0.8:1 to about 1:1, in a solvent such as tetrahydrofuran and in the presence of potassium t-butoxide to form the sulfide IV or IVA.

To form the sulfinyl and/or sulfonyl analogs (where n=1), sulfide derivative IV or IVA is subjected to oxidation, for example by reacting same with sodium periodate, in the presence of methanol and tetrahydrofuran, to form the sulfinyl derivative V or VA and the sulfonyl derivative VI or VIA. The above sulfinyl and sulfonyl derivatives may be separated by chromatography or other conventional separation procedures.

In the reaction sequence identified as "B", where in Formula I n is 2 to 4, the starting lower alkyl ester containing the hydroxymethyl group, that is, compound II, (prepared as described in U.S. Pat. No. 4,143,054) is used to form the aldehyde II' (where A is —CH=CH—) or IIA' (where A is —(CH$_2$)$_2$). Thus, to form aldehyde II' where A is —CH=CH—, compound II is subjected to a Collins oxidation, for example, by reacting II with chromium trioxide in pyridine. To form the aldehyde IIA' (where A is (CH$_2$)$_2$), compound II is reduced, for example with hydrogen over a palladium on carbon catalyst, to form hydroxymethyl compound IIA (where A is (CH$_2$)$_2$) and compound IIA is subjected to a Collins oxidation to form aldehyde IIA' (where A is (CH$_2$)$_2$).

The aldehyde II' or IIA' is used to prepare aldehyde VIII (where n is 2-4) by carrying out a homologation sequence, such as a Wittig reaction with (C$_6$H$_5$)$_3$P=CHOMe followed by hydrolysis, (n−1) times. The aldehyde VIII (where n is 2-4) is thus carried on to compounds of this invention where n is 2-4, that is (IV' where A is =CH=CH—)
(IVA' where A is (CH$_2$)$_2$)

by reducing aldehyde VIII employing a reducing agent such as sodium borohydride or sodium cyanoborohydride in a solvent such as methanol to form the alcohol ester IX which is subjected to a tosylation reaction as described above to form tosylate X which in turn is subjected to thioether formation by reaction with

R$^1$SH    A as described above to form sulfide IV' or IVA'.

The sulfinyl derivative (where n is 2 to 4) and sulfonyl derivatives (where n is 2 to 4) are prepared by subjecting sulfide IV' or IVA' to an oxidation reaction as described above to form a mixture of sulfinyl V' and/or VA', and sulfonyl VI' and/or VIA'.

The above sulfinyl and sulfonyl derivatives may be separated by chromatography or other convention separation procedures.

The esters IV, V, VI, IVA, VA, VIA, IV', V', VI', IVA', VA' and VIA' can be converted to the free acid, that is, to

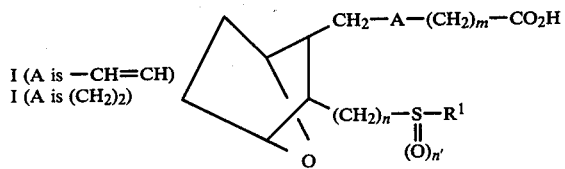

by treating the esters with an alkali metal hydroxide, such as lithium or sodium hydroxide to form the alkali metal salt Ia or Ib or Ia' or Ib', followed by neutralization with an acid, such as dilute hydrochloric acid or oxalic acid to form the acid IA, IB, I' or IA'.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

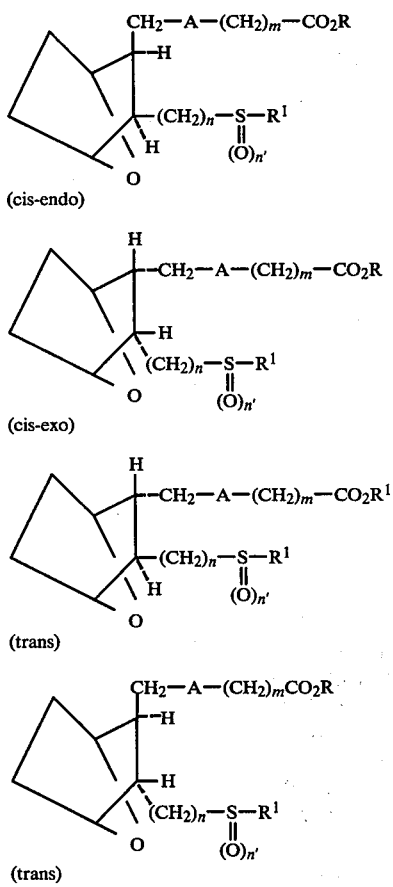

The nucleus in each of the compounds of the invention is depicted as

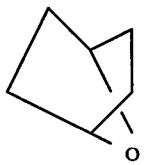

for matter of convenience; it will also be appreciated that the nucleus in the compounds of the invention may be depicted as

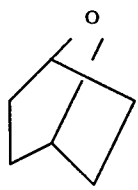

The compounds of this invention inhibit arachidonic acid-induced platelet aggregation and broncho-constriction.

The compounds of this invention are cardiovascular agents useful as platelet aggregation inhibitors, e.g., for treatment of thrombolytic disease, such as coronary or cerebral thromboses. They are also selective thromboxane $A_2$ receptor antagonists and synthetase inhibitors, e.g., having a vasodilatory effect for treatment of myocardial ischemic disease, such as angina pectoris. They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of this invention.

EXAMPLE 1

[1β,2α(5Z),3α,4β]-7-[3-[(Hexylthio)methyl]-7-oxabicyclo[2.2.1]hept-2-yl]-5-heptenoic acid, methyl ester

A.

[1β,2α(5Z),3α,4β]-7-[3-(Hydroxymethyl)-7-oxabicyclo[2.2.1]hept-2-yl]-5-heptenoic acid (a) A mixture of N-acetylpyridinium chloride was prepared by adding 9.6 ml (136 mmole) of acetyl chloride dropwise to 56 ml of pyridine. To this was added 5.0 g (27 mmole) of (exo)-3-(2-methoxyethenyl)-7-oxabicyclo[2.2.1]heptane-2-methanol dissolved in 5 ml of pyridine. The resulting mixture was stirred at room temperature for 1.5 hours and poured into brine. The product was extracted into ether (3×200 ml), the ether extracts were washed with 5% hydrochloric acid (2×400 ml) and brine (1×200 ml) and dried over sodium sulfate. Concentration yielded a yellow oil which was purified by passage through a short column of silica gel (150 ml) with dichloromethane, yield 4.42 g of an oil.

(b) To a solution of 4.42 g (19.6 mmole) of the oil in 500 ml of tetrahydrofuran containing 50 ml of water was added 31.1 g (97.8 mmole) of mercuric acetate. The yellow suspension which formed was stirred for 10 minutes and then the entire mixture was poured into a solution containing 200 g of potassium iodide in 2 l. of water. Upon shaking, the yellow color disappeared and the mixture was extracted with benzene (3×500 ml). The combined benzene extracts were washed with potassium iodide solution and brine and dried over sodium sulfate. Concentration yielded 3.7 g of material which crystallized on standing in an ice box.

(c) A Wittig reagent was prepared in dimethyl sulfoxide (dried over calcium hydride) by adding a solution of sodium methylsulfinylmethide (prepared by heating 300 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of the product of part (b) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gives an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 500 g of silica gel with 50/50 ethyl acetate-hexane as the eluant which gave 600 mg of acid which crystallized on standing. This was recrystallized twice from ethyl acetate-cyclohexane to yield 320 mg of [1$\beta$,2$\alpha$(5Z),3$\alpha$,4$\beta$[-7-[3-(hydroxymethyl)-7-oxabicyclo[2.2.1]hept-2-yl]-5-heptenoic acid.

B.
[1$\beta$,2$\alpha$(5Z),3$\alpha$,4$\beta$]-7-[3-(p-Toluenesulfonyl-oxymethyl)-7-oxabicyclo[2.2.1]hept-2-yl]-5-heptenoic acid, methyl ester To a solution of 300 mg (1.12 mmol) of alcohol ester from Part A in 4 ml of dry pyridine was added 427 mg (2.24 mmol) of tosyl chloride. The mixture was stirred at room temperature under an argon atmosphere for 10 hours. The reaction mixture was diluted with 300 ml of ether, washed with 1N aqueous HCl solution (3×100 ml), and 0.5N aqueous NaOH solution (3×100 ml). The ether layer was dried over anhydrous magnesium sulfate and concentrated in vacuo. Purification was effected by flash chromatography on 30 g of silica gel 60 using 50% hexane in ether as eluant to give 450 mg of title compound (95%). TLC:silica gel, 4% CH$_3$OH in CH$_2$Cl$_2$, R$_f$=0.80, iodine.

C.
]1$\beta$,2$\alpha$(5Z),3$\alpha$,4$\beta$]-7-[3-[(Hexylthio)methyl]-7-oxabicyclo[2.2.1]hept-2-yl]-5-heptenoic acid, methyl ester To a solution of 132 mg (1.17 mmol) of potassium t-butoxide in 10 ml of dry THF under argon was added 378 mg (3.21 mmol) of 1-hexanethiol. To this mixture was added a solution of 450 mg (1.07 mmol) of Part B tosylate in 5 ml of THF. The reaction mixture was stirred at room temperature under argon for 2.5 hours and then heated to reflux for 5.5 hours. The cooled reaction was diluted with 300 ml of ether and poured into 100 ml of saturated NaHCO$_3$ solution. The aqueous layer was extracted with ether (2×100 ml). The combined ether extracts (500 ml) were washed with 0.5N aqueous sodium hydroxide (2×100 ml), brine (100 ml), and then dried (MgSO$_4$), filtered and concentrated in vacuo to give 0.55 g of crude oil. Purification was effected by chromatography on 25.2 g of silica gel 60 using 5:1 pet ether:ether as eluant to give 328 mg of title product as an oil (84%). TLC=silica gel, petroleum ether:ether 3:2, R$_f$=0.55, iodine.

EXAMPLE 2

[1$\beta$,2$\alpha$(5Z),3$\alpha$,4$\beta$]-7-[3-[(Hexylthio)methyl]-7-oxabicyclo[2.2.1]hept-2-yl]-5-heptenoic acid To a stirred solution of 328 mg (0.89 mmol) of the Example 1 methyl ester in 43.8 ml of THF and 6.67 ml of H$_2$O under argon was added 8.40 ml of 1N aqueous lithium hydroxide solution. This mixture was purged with argon vigorously for 20 minutes and stirred at room temperature for 12.5 hours. The reaction mixture was acidified to pH 4 by the addition of 1N aqueous HCl solution and poured into 50 ml of saturated NaCl solution. The resulting solution was saturated with solid NaCl and extracted with EtOAc (4×50 ml). The combined EtOAc extracts were dried (MgSO$_4$), filtered and concentrated in vacuo to give 295 mg of crude acid. Purification was effected by flash chromatography on 25 g of siliCAR CC-7 using 2:3 petroleum ether:ether as eluant to give title product (250 mg, 79%) as an oil. TLC:silica gel, 2:3 petroleum ether:ether, R$_f$=0.25, iodine.

Anal. Calc'd for C$_{20}$H$_{34}$O$_3$S: C, 67.80; H, 9.61; S, 9.04 Found: C, 67.80; H, 9.85; S, 9.14

EXAMPLE 3

(1$\beta$, 2$\alpha$,3$\alpha$,4$\beta$)-7-[3-[(Hexylthio)methyl]-7-oxabicyclo[2.2.1]hept-2-yl]heptanoic aicd, methyl ester A.
(1$\beta$,2$\alpha$,3$\alpha$,4$\beta$)-7-[3-(Hydroxymethyl)-7-oxabicyclo[2.2.1]hept-2-yl]heptanoic acid methyl ester To 800 mg (3.0 mmole) of the [1$\beta$,2$\alpha$(5Z),-3$\alpha$,4$\beta$]-7-[3-(hydroxymethyl)-7-oxabicyclo[2.2.1]-hept-2-yl]-5-heptenoic acid, methyl ester as prepared in Example 1, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.
(1$\beta$,2$\alpha$,3$\alpha$,4$\beta$)-7-[3-[(Hexylthio)methyl]-7-oxabicyclo[2.2.1]hept-2-yl]heptanoic acid, methyl ester Following the procedure of Example 1 except substituting the Part A alcohol-ester for the Example 1A alcohol ester, the title product is obtained.

EXAMPLE 4

(1$\beta$,2$\alpha$,3$\alpha$,4$\beta$)-7-[3-[(Hexylthio)methyl]-7-oxabicyclo[2.2.1]hept-2-yl]-5-heptanoic acid Following the procedure of Example 2 except substituting the Example 3 methyl ester for the Example 2 methyl ester, the title acid is obtained.

EXAMPLE 5

]1$\beta$,2$\alpha$(5Z),3$\beta$,4$\beta$]-7-[3-[(Penthylthio)methyl[-7-oxabicyclo[2.2.1]hept-2-yl]-5-heptenoic acid, methyl ester A.
[1$\beta$,2$\alpha$(5Z),3$\beta$,4$\beta$[-7-[3-(p-Toluenesulfonyloxymethyl)-7-oxabicyclo[2.2.1]hept-2-yl]-5-heptenoic acid, methyl ester To a solution of 300 mg (1.12 mmol) of [1$\beta$,2$\alpha$(5Z),3$\beta$,4$\beta$]-7-[3-(hydroxymethyl)-7-oxabicyclo[2.2.1]hept-2-yl]-5-heptenoic acid, methyl ester prepared as described in U.S. Pat. No. 4,143,054 in 4 ml of dry pyridine is added 427 mg (2.24 mmol) of tosyl chloride. The mixture is stirred at room temperature under an argon atmosphere for 10 hours. The reaction mixture is diluted with 300 ml of ether, washed with 1N aqueous HCl solution (3×100 ml). The ether layer is dried over anhydrous magnesium sulfate and concentrated in vacuo. Purification is effected by flash chromatography on 30 g of silica gel 60 using 50% hexane in ether as eluant to give 450 mg of title A compound.

B.
[1β,2α(5Z),3β,4β]-7-[3-[(Pentylthio)methyl]-7-oxabicyclo[2.2.1]hept-2-yl]-5-heptenoic acid, methyl ester To a solution of 132 mg (1.17 mmol) of potassium t-butoxide in 10 ml of dry THF under argon is added 378 mg (3.21 mmol) of 1-pentanethiol. To this mixture is added a solution of 450 mg (1.07 mmol) of Part A tosylate in 5 ml of THF. The reaction mixture is stirred at room temperature under argon for 2.5 hours and then heated to reflux for 5.5 hours. The cooled reaction is diluted with 300 ml of ether and poured into 100 ml of saturated NaHCO$_3$ solution. The aqueous layer is extracted with ether (2×100 ml). The combined ether extracts (500 ml) are washed with 0.5N aqueous sodium hydroxide (2×100 ml), brine (100 ml), and then dried (MgSO$_4$), filtered and concentrated in vacuo to give 0.55 g of crude oil. Purification was effected by chromatography on 25.2 g of silica gel 60 using 5:1 pet. ether:ether as eluant to give 328 mg of title compound.

EXAMPLE 6

[1β,2α(5Z),3β,4β]-7-[3-[(Pentylthio)methyl]-7-oxabicyclo[2.2.1]hept-2-yl]-5-heptenoic acid To a stirred solution of 328 mg (0.89 mmol) of Example 5 methyl ester in 43.8 ml of THF and 6.67 ml of H$_2$O under argon is added 8.40 ml of 1N aqueous lithium hydroxide solution. This mixture is purged with argon vigorously for 20 minutes and stirred at room temperature for 12.5 hours. The reaction mixture is acidified to pH 4 by the addition of 1N aqueous HCl solution and poured into 50 ml of saturated NaCl solution. The resulting solution is saturated with solid NaCl and extracted with EtOAc (4×50 ml). The combined EtOAc extracts are dried (MgSO$_4$), filtered and concentrated in vacuo to give 295 mg of crude acid. Purification is effected by flash chromatography on 25 g of siliCAR CC-7 using 2:3 petroleum ether:ether as eluant to give the acid.

EXAMPLE 7

[1β,2α(5Z),3α,4β]-7-[3-[(Methylthio)methyl]-7-oxabicyclo[2.2.1]hept-2-yl]-5-heptenoic acid Following the procedure of Examples 1 and 2 except substituting methyl mercaptan for 1-hexanethiol, the title compound is obtained.

EXAMPLE 8

[1β,2α(5Z),3β,4β]-7-[3-[(Propylthio)methyl]-7-oxabicyclo[2.2.1]hept-2-yl]-5-heptenoic acid Following the procedure of Examples 5 and 6 except substituting propylmercaptan for 1-pentanethiol, the title compound is obtained.

EXAMPLE 9

(1β,2α,3α,4β)-7-[3-(Butylthio)methyl]-7-oxabicyclo[2.2.1]hept-2-yl]heptanoic acid Following the procedure of Examples 3 and 4 except substituting butylmercaptan for 1-hexanethiol, the title compound is obtained.

EXAMPLE 10

[1β,2α(5Z),3α,4β]-7-[3-[(Octylthio)methyl]-7-oxabicyclo[2.2.1]hept-2-yl]-5-heptenoic acid Following the procedure of Examples 1 and 2 except substituting 1-octanethiol for 1-hexanethiol, the title compound is obtained.

EXAMPLE 11

[1β,2α(5Z),3α,4β]-7-[3-[(Phenylthio)methyl[-7-oxabicyclo[2.2.1]hept-2-yl]-5-heptenoic acid Following the procedure of Examples 1 and 2 except substituting phenylmercaptan for 1-hexanethiol, the title compound is obtained.

EXAMPLE 12

(1β,2α,3α,4β)-7-[3-[(Phenylthio)methyl]-7-oxabicyclo[2.2.1]hept-2-yl]heptanoic acid Following the procedure of Examples 3 and 4 except substituting phenylmercaptan for 1-hexanethiol, the title compound is obtained.

EXAMPLE 13

[1β,2α(5Z),3α,4β]-7-[3-[(Ethylthio)methyl]-7-oxabicyclo[2.2.1]hept-2-yl]-5-heptenoic acid Following the procedure of Examples 1 and 2 except substituting ethylmercaptan for 1-hexanethiol, the title compound is obtained.

EXAMPLE 14

[1β,2α(5Z),3β,4β]-7-[3-[(Phenylthio)methyl]-7-oxabicyclo[2.2.1]hept-2-yl]-5-heptenoic acid Following the procedure of Examples 5 and 6 except substituting phenylmercaptan for 1-pentanethiol, the title product is obtained.

EXAMPLE 15

[1β,2α(5Z),3β,4β]-7-[3-[(Benzylthio)methyl]-7-oxabicyclo[2.2.1]hept-2-yl]-5-heptenoic acid Following the procedure of Examples 5 and 6 except substituting benzylmercaptan for 1-pentanethiol, the title product is obtained.

EXAMPLE 16

(1β,2α,3α,4β)-7-[3-[(Benzylthio)methyl]-7-oxabicyclo[2.2.1]hept-2-yl]heptanoic acid Following the procedure of Examples 3 and 4 except substituting benzylmercaptan for 1-hexanethiol, the title product is obtained.

EXAMPLE 17

[1β,2α(5Z),3α,4β]-7-[3-[(Cyclohexylthio)methyl]-7-oxabicyclo[2.2.1]hept-2-yl]-5-heptenoic acid Following the procedure of Examples 1 and 2 except substituting cyclohexylmercaptan for 1-hexanethiol, the title product is obtained.

EXAMPLE 18

[1β,2α(5Z),3β,4β]-7-[3(Cyclopentylthio)methyl]-7-oxabicyclo[2.2.1]hept-2-yl]-5-heptenoic acid Following the procedure of Examples 5 and 6 except substituting cyclopentylmercaptan for 1-pentanethiol, the title product is obtained.

EXAMPLE 19

(1β,2α,3α,4β)-7-[3-[(Cyclohexylthio)methyl]-7-oxabicyclo[2.2.1]hept-2-yl]heptanoic acid Following the procedure of Examples 3 and 4 except substituting cyclohexylmercaptan for 1-hexanethiol, the title product is obtained.

EXAMPLE 20

[1β,2α(5Z),3α,4β]-7-[3-[2-(Hexylthio)ethyl]-7-oxabicyclo[2.2.1]hept-2-yl[-5-heptenoic acid

A.

[1β,2α(5Z),3α,4β]-7-[3-(2-Oxo)ethyl-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride (($C_6H_5)_3P^+-CH_2OCH_3Cl^-$) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]-hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated $NH_4Cl$, and extracted with ether (4×200 ml). The combined ether phases were washed with NaCl, saturated solution, and dried ($MgSO_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1β,2α(5Z),3α,4β]-7-[3-(2-oxo)ethyl-7-oxabicycklo[2.2.1]hept-2-yl]-5-heptenoic acid, methyl ester, (B) [1β,2α(5Z),3α,4β]-7-[3-(2-methoxy)-ethendiyl-7-oxabicyclo[2.2.1.-]hept-2-yl]-5-heptenoic acid, methyl ester, and (C) [1β,2α(5Z),3α,4β]-7-[3-(2,2-dimethoxy)ethyl-7-oxabicyclo[2.2.1]hept-2-yl]-5-heptenoic acid, methyl ester.

Compounds (B) and (C) are each treated with trifluoroacetic acid to convert each to compound (A).

B.

[1β,2α(5Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with $NaBH_4$ (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated $KHCO_3$, saturated NaCl and dried ($MgSO_4$). The ether is evaporated to yield the title B compound.

C.

[1β,2α(5Z),3α,4β]-7-[3-[2-(Hexylthio)-ethyl]-7-oxabicyclo[2.2.1]hept-2-yl]-5-heptenoic acid Following the procedure of Examples 1 and 2 except substituting the above part B alcohol for the alcohol used in Example 1, the title compound is obtained.

EXAMPLE 21

[1β,2α(5Z),3β,4β]-7-[3-[2-(Hexylthio)ethyl]-7-oxabicyclo[2.2.1]hept-2-yl]-5-heptenoic acid Following the procedure of Example 20, except substituting [1β,2α(5Z),3β,4β]-7-[3-formyl-7-oxabicyclo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title compound is obtained.

EXAMPLE 22

(1β,2α,3α,4β)-7-[3-[2-(Hexylthio)ethyl]-7-oxabicyclo[2.2.1]hept-2-yl]heptanoic acid Following the procedure of Example 21 except substituting (1β,2α,3α,4β)-7-[3-formyl-7-oxabicyclo[2.2.1-]hept-2-yl]heptanoic acid, methyl ester for [1β,2α(5Z)-,3α,4β]-7-[3-formyl-7-oxabicyclo[2.2.1]-hept-2-yl]-5-heptenoic acid, methyl ester, the title compound is obtained.

EXAMPLE 23

[1β,2α(5Z),3α,4β]-7-[3-[2-(Phenylthio)ethyl]-7-oxabicyclo[2.2.1]hept-2-yl]-5-heptenoic acid Following the procedure of Example 20 except substituting phenylmercaptan for 1-hexanethiol, the title compound is obtained.

EXAMPLE 24

[1β,2α(5Z),3β,4β]-7-[3-[2-(Phenylthio)ethyl]-7-oxabicyclo[2.2.1]hept-2-yl]-5-heptenoic acid Following the procedure of Example 21 except substituting phenylmercaptan for 1-hexanethiol, the title compound is obtained.

EXAMPLE 25

(1β,2α,3α,4β)-7-[7-[3-[2-(Phenylthio)ethyl]-7-oxabicyclo[2.2.1]hept-2-yl]heptanoic acid Following the procedure of Example 22 except substituting phenylmercaptan for 1-hexanethiol, the title compound is obtained.

EXAMPLE 26

[1β,2α(5Z),3α,4β]-7-[3-[2-(Benzylthio)ethyl]-7-oxabicyclo[2.2.1]hept-2-yl]-5-heptenoic acid Following the procedure of Example 20 except substituting benzylmercaptan for 1-hexanethiol, the title compound is obtained.

EXAMPLE 27

[1β,2α(5Z),3β,4β]-7-[3-[2-(Benzylthio)ethyl]-7-oxabicyclo[2.2.1]hept-2-yl]-5-heptenoic acid Following the procedure of Example 21 except substituting benzylmercaptan for 1-hexanethiol, the title compound is obtained.

EXAMPLE 28

[1β,2α(5Z),3α,4β]-7-[3-[2-(Cyclopentyl)thio)ethyl]-7-oxabicylo[2.2.1]hept-2-yl]heptenoic acid Following the procedure of Example 20 except substituting cyclopentylmercaptan for 1-hexanethiol, the title compound is obtained.

EXAMPLE 29

[1β,2α(5Z),3α,4β]-7-[3-[2-(Cyclohexylthio)ethyl]-7-oxabicyclo[2.2.1]hept-2-yl]-5-heptenoic acid Following the procedure of Example 20 except substituting cyclohexylmercaptan for 1-hexanethiol, the title product is obtained.

EXAMPLE 30

[1β,2α(5Z),3α,4β]-7-[3-[4-(Hexylthio)butyl]-7-oxabicyclo[2.2.1]hept-2-yl]-5-heptenoic acid

A.

[1β,2α(5Z),3α,4β]-7-[3-(3-Oxo)propyl-7-oxabicyclo[2.2.1]hept-2-yl]-5-heptenoic acid, methyl ester Following the procedure of Example 20, part A except substituting [1β,2α(5Z),3α,4β[-7-[3-(2-oxo)-ethyl-7-oxabicylo[2.2.1]hept-2-yl]-5-heptenoic acid, methyl ester for [1β,2α(5Z),3α,4β]-7-[3-formyl-7-oxabicyclo[2.2.1]hept-2-yl]-5-heptenoic acid, methyl ester, the title A compound is obtained.

B.

[1β,2α(5Z),3α,4β]-7-[3-(4-Oxo)butyl-7-oxabicylo[2.2.1-]hept-2-yl]-5-heptenoic acid, methyl ester Following the procedure of Example 20, part A, except substituting the aldehyde from part A above, for [1β,2α(5Z),3α,4β]-7-[3-formyl-7-oxabicyclo[2.2.1]hept-2-yl]-5-heptenoic acid, methyl ester, the title B aldehyde is obtained.

C.

[1β,2α(5Z),3α,4β]-7-[3-(4-Hydroxybutyl)-7-oxabicyclo[2.2.1]hept-2-yl]-5-heptenoic acid, methyl ester Following the procedure of Example 20, part B, except substituting the title B aldehyde for [1β,2α(5Z)-,3α,4β]-7-[3-(2-oxo)ethyl]-7-oxabicyclo[2.2.1]hept-2-yl]-5-heptenoic acid, methyl ester, the title C alcohol is obtained.

D.

[1β,2α(5Z),3α,4β]-7-[3-[4-(Hexylthio)-butyl]-7-oxabicyclo[2.2.1]hept-2-yl]-5-heptenoic acid Following the procedure of Examples 1 and 2, except substituting the above part C alcohol for the alcohol used in Example 1, the title compound is obtained.

EXAMPLE 31

[1β,2α(5Z),3α,4β]-7-[3-[4-(Cyclohexylthio)butyl]-7-oxabicyclo[2.2.1]hept-2-yl]-5-heptenoic acid Following the procedure of Example 30 except substituting cyclohexylmercaptan for 1-hexanethiol, the title compound is obtained.

EXAMPLE 32

[1β,2α(5Z),3α,4β]-7-[3-[4-(Phenylthio)butyl]-7-oxabicyclo[2.2.1]hept-2-yl]-5-heptenoic acid Following the procedure of Example 30 except substituting phenylmercaptan for 1-hexanethiol, the title compound is obtained.

EXAMPLE 33

[1β,2α(5Z),3α,4β]-7-[3-[4-(Benzylthio)butyl]-7-oxabicyclo[2.2.1]hept-2-yl]heptenoic acid Following the procedure of Example 30 except substituting benzylmercaptan for 1-hexanethiol, the title compound is obtained.

EXAMPLES 34, 35 and 36

[1β,2α(5Z),3α,4β]-7-[3-[(Hexylsulfinyl)methyl]-7-oxabicyclo[2.2.1]hept-2-yl]-5-heptenoic acid, methyl ester (fast moving isomer),
[1β,2α(5Z),3α,4β]-7-[3-[(Hexylsulfinyl)methyl]-7-oxabicyclo[2.2.1]hept-2-yl]-5-heptenoic acid, methyl ester (slow moving isomer) and
[1β,2α(5Z),3α,4β]-7-[3-[(Hexylsulfonyl)-methyl]-7-oxabicyclo[2.2.1]hept-2-yl]-5-heptenoic acid, methyl ester To a solution of 634 mg (1.72 mmol) of [1β,2α(5Z)-,3α,4β]-7-[3-[(hexylthio)methyl]-7-oxabicyclo[2.2.1-]hept-2-yl]-5-heptenoic acid, methyl ester (prepared as described in Example 1) in 6.78 ml of methanol at 0° C. was added dropwise over 4 minutes 8.37 ml of 0.5M aqueous sodium periodate solution. Tetrahydrofuran (2 ml) was then added and the resulting reaction mixture was stirred at room temperature for 15 hours. A white precipitate was removed by filtration and washed with ether (3×50 ml). The filtrate was washed with 60 ml of saturated aqueous NaHCO3 solution and dried over anhydrous magnesium sulfate. Concentration in vacuo afforded 648 mg of an oily crude product. This was chromatographed on 54.16 g of silica gel 60 using 0.5–1.0% CH3OH in CH2Cl2 as eluent. This gave FMI (fast moving isomer) sulfoxide (Example 34) (211 mg, 32%), SMI (slow moving isomer) sulfoxide (Example 35) (142 mg, 21%) and sulfone (Example 36) (165 mg, 24%). These products were oils which solidified on storage in the freezer. TLC=silica gel, 2% (CH3OH/CH2Cl2, RF: Example 34 sulfoxide, 0.28; Example 35 sulfoxide, 0.21; Example 36 sulfone, 0.74; iodine.

EXAMPLE 37

[1β,2α(5Z),3α,4β]-7-[3-[(Hexylsulfonyl)methyl]-7-oxabicyclo[2.2.1]hept-2-yl]-5-heptenoic acid To a stirred solution of 165 mg (0.41 mmol) of [1β,2α(5Z),3α,4β]-7-8  3-(hexylsulfonyl)methyl]-7-oxabicyclo[2.2.1]hept-2-yl]-5-heptenoic acid, methyl ester (Example 36) in 20.3 ml of THF and 3.09 ml of H2O under argon was added 3.90 ml of 1N aqueous lithium hydroxide solution. This mixture was purged with argon vigorously for 10 minutes and stirred at room temperature for 6 hours. The reaction mixture was acidified to pH 4 by addition of 1N aqueous HCl solution and poured into 30 ml of saturated NaCl solution. The resulting solution was saturated with solid NaCl and extracted with EtOAc (4×50 ml). The combined EtOAc extracts were dried (MgSO4), filtered and concentrated in vacuo to give 165 mg of crude acid.

Purification was effected by flash chromatography on 20 g of silica gel 60 using 3% CH₃OH in CH₂Cl₂ as eluant. This afforded title acid (145 mg, 91%) which solidified on storage in the freezer. TLC=silica gel, 4% CH₃OH/CH₂Cl₂, $R_f$ 0.32, iodine.

Anal. Calcd for $C_{20}H_{34}O_5S$: C, 62.18; H, 8.81; S, 8.29
Found: C, 61.99; H, 9.01; S, 8.33

EXAMPLE 38

[1β,2α(5Z),3α,4β]-7-[3-[(Hexylsulfinyl)methyl]-7-oxabicyclo[2.2.1]hept-2-yl]-5-heptenoic acid (fast moving isomer)

To a stirred solution of 211 mg (0.55 mmol) of [1β,2α(5Z),3α,4β]-7-[3-[(hexylsulfinyl)methyl]-7-oxabicylo[2.2.1]hept-2-yl]-5-heptenoic acid, methyl ester (fast moving isomer) prepared in Example 34 in 27.0 ml of THF and 4.11 ml of H₂O under argon was added 5.19 ml of 1N aqueous lithium hydroxide solution. This mixture was purged with argon vigorously for ten minutes and stirred at room temperature for 6 hours. The reaction mixture was acidified to pH 4 by addition of 1N aqueous HCl solution and poured into 50 ml of saturated NaCl solution. The resulting solution was saturated with solid NaCl and extracted with EtOAc (4×100 ml). The combined EtOAc extracts were dried (MgSO₄), filtered and concentrated in vacuo to give 216 mg of crude acid. Purification was effected by flash chromtography on 20.2 g of silica gel 60 using 3% CH₃OH in CH₂Cl₂ as eluant to give the title acid (172 mg, 85%) as a white solid. TLC=silica gel, 4% CH₃OH/CH₂Cl₂, $R_f$ 0.10, iodine.

Anal. Calcd for $C_{20}H_{34}O_4S$: C, 64.83; H, 9.25; S, 8.65
Found: C, 64.71; H, 9.17; S, 8.55

EXAMPLE 39

[1β,2α(5Z),3α,4β]-7-[3-[(Hexylsulfinyl)methyl]-7-oxabicyclo[2.2.1]hept-2-yl]-5-heptenoic acid (slow moving isomer)

To a stirred solution of 142 mg (0.37 mmol) of [1β,2α(5Z),3α,4β]-7-[3-[(hexylsulfinyl)methyl]-7-oxabicyclo[2.2.1]hept-2-yl]-5-heptenoic acid, methyl ester (slow moving isomer) prepared as described in Example 35 in 18.2 ml of THF and 2.77 ml of H₂O under argon was added 3.50 ml of 1N aqueous lithium hydroxide solution. This mixture was purged with argon vigorously for 15 minutes and stirred at room temperature for 4 hours and 40 minutes. The reaction mixture was acidified to pH 4 by addition of 1N aqueous HCl solution and poured into 30 ml of saturated NaCl solution. The resulting solution was saturated with solid NaCl and extracted with EtOAc (3×70 ml). The combined EtOAc extracts were dried (MgSO₄), filtered and concentrated in vacuo to give 152 mg of crude acid. Purification was effected by flash chromatography on 20.8 g of silica gel 60 using 4% CH₃OH in CH₂Cl₂ as eluant to give title acid (116 mg, 85%). TLC: silica gel, 4% CH₃OH/CH₂Cl₂, $R_f$ 0.6, iodine.

Anal. Calcd for $C_{20}H_{34}O_4S$: C, 64.83; H, 9.25; S, 8.65
Found: C, 64.44; H, 9.15; S, 8.58

EXAMPLE 40

[1β,2α(5Z),3α,4β]-7-[3-[(Methylsulfinyl)methyl]-7-oxabicyclo[2.2.1]hept-2-yl]-5-heptenoic acid (fast moving isomer)

Following the procedure of Examples 1, 34 and 38 except substituting methyl mercaptan for 1-hexanethiol, the title compound is obtained.

EXAMPLE 41

[1β,2α(5Z),3α,4β]-7-[3-[(Octylsulfinyl)methyl]-7-oxabicyclo[2.2.1]hept-2-yl]-5-heptenoic acid (slow moving isomer)

Following the procedure of Examples 1, 34 and 39 except substituting 1-octanethiol for 1-hexanethiol, the title compound is obtained.

EXAMPLE 42

[1β,2α(5Z),3β,4β]-7-[3-[(Phenylsulfinyl)methyl]-7-oxabicyclo[2.2.1]hept-2-yl]-5-heptenoic acid (fast moving isomer)

Following the procedure of Examples 5, 34 and 38 except substituting phenylmercaptan for 1-pentanethiol, the title compound is obtained.

EXAMPLE 43

[1β,2α(5Z),3α,4β]-7-[3-[(Ethylsulfinyl)methyl]-7-oxabicyclo[2.2.1]hept-2-yl]-5-heptenoic acid (slow moving isomer)

Following the procedure of Example 5, 34 and 39 except substituting ethylmercaptan for 1-pentanethiol, the title compound is obtained.

EXAMPLE 44

(1β,2α,3α,4β)-7-[3-[(Heptylsulfinyl)methyl]-7-oxabicyclo[2.2.1]hept-2-yl]heptanoic acid (fast moving isomer)

Following the procedure of Examples 3, 34 and 38 except substituting 1-heptanethiol for 1-hexanethiol, the title compound is obtained.

EXAMPLE 45

[1β,2α(5Z),3α,4β]-7-[3-[(Benzylsulfinyl)methyl]-7-oxabicyclo[2.2.1]hept-2-yl]-5-heptenoic acid Following the procedure of Examples 1, 34 and 38 except substituting benzylmercaptan for 1-hexanethiol, the title compound is obtained.

EXAMPLE 46

[1β,2α(5Z),3β,4β]-7-[3-[(Benzylsulfinyl)methyl]-7-oxabicyclo[2.2.1]hept-2-yl]-5-heptenoic acid (slow moving isomer)

Following the procedure of Examples 5, 34 and 39 except substituting benzylmercaptan for 1-pentanethiol, the title compound is obtained.

EXAMPLE 47

[1β,2α(5Z),3α,4β]-7-[3-[(Cyclohexylsulfinyl)methyl]-7-oxabicyclo[2.2.1]hept-2-yl]-5-heptenoic acid (fast moving isomer)

Following the procedure of Examples 1, 34 and 38 except substituting cyclohexylmercaptan for 1-hexanethiol, the title compound is obtained.

EXAMPLE 48

[1β,2α(5Z),3α,4β]-7-[3-[(Cyclopentylsulfinyl)-methyl]-7-oxabicyclo[2.2.1]hept-2-yl]-5-heptenoic acid (fast moving isomer)

Following the procedure of Examples 1, 34 and 38 except substituting cyclopentylmercaptan for 1-hexanethiol, the title compound is obtained.

EXAMPLE 49

[1β,2α(5Z),3α,4β]-7-[3-[(Octylsulfonyl)methyl]-7-oxabicyclo[2.2.1]hept-2-yl]-5-heptenoic acid Following the procedure of Examples 1, 34 and 37 except substituting octylmercaptan for 1-hexanethiol, the title compound is obtained.

EXAMPLE 50

[1β,2α(5Z),3α,4β]-7-[3-[(Propylsulfonyl)methyl]-7-oxabicyclo[2.2.1]hept-2-yl]-5-heptenoic acid Following the procedure of Examples 1, 34 and 37 except substituting propylmercaptan for 1-hexanethiol, the title compound is obtained.

EXAMPLE 51

[1β,2α(5Z),3α,4β]-7-[3-[(Phenylsulfonyl)methyl]-7-oxabicyclo[2.2.1]hept-2-yl]-5-heptenoic acid Following the procedure of Examples 1, 34 and 37 except substituting phenylmercaptan for 1-hexanethiol, the title compound is obtained.

EXAMPLE 52

[1β,2α(5Z),3α,4β]-7-[3-[(Benzylsulfonyl)methyl]-7-oxabicyclo[2.2.1]hept-2-yl]-5-heptenoic acid Following the procedure of Examples 1, 34 and 37 except substituting benzylmercaptan for 1-hexanethiol, the title compound is obtained.

EXAMPLE 53

[1β,2α(5Z),3α,4β]-7-[3-[(Cyclohexylsulfonyl)methyl]-7-oxabicyclo[2.2.1]hept-2-yl]-5-heptenoic acid Following the procedure of Examples 1, 34 and 37 except substituting cyclohexylmercaptan for 1-hexanethiol, the title compound is obtained.

EXAMPLE 54

[1β,2α(5Z),3β,4β]-7-[3-[(Heptylsulfonyl)methyl]-7-oxabicyclo[2.2.1]hept-2-yl]-5-heptenoic acid Following the procedure of Examples 5, 34 and 37 except substituting 1-heptanethiol for 1-pentanethiol, the title compound is obtained.

EXAMPLE 55

[1β,2α(5Z),3β,4β]-7-[3-[(Benzylsulfonyl)methyl]-7-oxabicyclo[2.2.1]hept-2-yl]-5-heptenoic acid Following the procedure of Examples 5, 34 and 37 except substituting benzylmercaptan for 1-pentanethiol, the title compound is obtained.

EXAMPLE 56

[1β,2α(5Z),3β,4β]-7-[3-[(Cyclopentylsulfonyl)methyl]-7-oxabicyclo[2.2.1]hept-2-yl]-5-heptenoic acid Following the procedure of Examples 5, 34 and 37 except substituting cyclopentylmercaptan for 1-pentanethiol, the title compound is obtained.

EXAMPLE 57

[1β,2α(5Z),3β,4β]-7-[3-[(Phenylsulfonyl)methyl]-7-oxabicyclo[2.2.1]hept-2-yl]-5-heptenoic acid Following the procedure of Examples 5, 34 and 37 except substituting phenylmercaptan for 1-pentanethiol, the title compound is obtained.

EXAMPLE 58

(1β,2α,3α,4β)-7-[3-[(Cyclopropylsulfinyl)methyl]-7-oxabicyclo[2.2.1]hept-2-yl]heptanoic acid Following the procedure of Examples 3, 34 and 38 except substituting cyclopropylmercaptan for 1-hexanethiol, the title compound is obtained.

EXAMPLE 59

(1β,2α,3α,4β)-7-[3-[(Benzylsulfinyl)methyl]-7-oxabicyclo[2.2.1]hept-2-yl]heptanoic acid Following the procedure of Examples 3, 34 and 38 except substituting benzylmercaptan for 1-hexanethiol, the title compound is obtained.

EXAMPLE 60

[1β,2α(5Z),3α,4β]-7-[3-[2-(Pentylsulfinyl)ethyl]-7-oxabicyclo[2.2.1]hept-2-yl]-5-heptenoic acid Following the procedure of Examples 20, 1, 34 and 38 except substituting 1-pentanethiol for 1-hexanethiol, the title compound is obtained.

EXAMPLE 61

[1β,2α(5Z),3α,4β]-7-[3-[2-(Phenylsulfinyl)ethyl]-7-oxabicyclo[2.2.1]hept-2-yl]-5-heptenoic acid Following the procedure of Examples 20, 1, 34 and 37 except substituting phenylmercaptan for 1-hexanethiol, the title compound is obtained.

EXAMPLE 62

[1β,2α(5Z),3α,4β]-7-[3-[2-(Cyclohexylsulfonyl)ethyl]-7-oxabicyclo[2.2.1]hept-2-yl]-5-heptenoic acid Following the procedure of Examples 20, 1, 34 and 37 except substituting cyclohexylmercaptan for 1-hexanethiol, the title compound is obtained.

EXAMPLE 63

[1β,2α(5Z),3α,4β]-7-[3-[2-(Benzylsulfinyl)ethyl]-7-oxabicyclo[2.2.1]hept-2-yl]-5-heptenoic acid Following the procedure of Examples 20, 1, 34 and 38 except substituting benzylmercaptan for 1-hexanethol, the title compound is obtained.

EXAMPLE 64

[1β,2α(5Z),3β,4β]-7-[3-[2-(Butylsulfonyl)ethyl]-7-oxabicyclo[2.2.1]hept-2-yl]-5-heptenoic acid Following the procedure of Examples 20, 5, 34 and 37 except substituting butylmercaptan for 1-pentanethiol, the title compound is obtained.

EXAMPLE 65

[1β,2α(5Z),3β,4β]-7-[3-[2-(Phenylsulfinyl)ethyl]-7-oxabicyclo[2.2.1]hept-2-yl]-5-heptenoic acid Following the procedure of Examples 20, 5, 34 and 38 except substituting phenylmercaptan for 1-pentanethiol, the title compound is obtained.

EXAMPLE 66

[1β,2α(5Z),3β,4β]-7-[3-[2-(Benzylsulfinyl)ethyl]-7-oxabicyclo[2.2.1]hept-2-yl]-5-heptenoic acid Following the procedure of Examples 20, 5, 34 and 38 except substituting benzylmercaptan for 1-pentanethiol, the title compound is obtained.

EXAMPLE 67

[1β,2α(5Z), 3β,4β]-7-[3-[2-(Cycloheptylsulfonyl)-ethyl]-7-oxabicyclo[2.2.1]hept-2-yl]-5-heptenoic acid Following the procedure of Examples 20, 5, 34 and 37 except substituting cycloheptylmercaptan for 1-pentanethiol, the title compound is obtained.

EXAMPLE 68

(1β,2α,3α,4β)7-[3-[2-(Pentylsulfonyl)ethyl]-7-oxabicyclo[2.2.1]hept-2-yl]heptanoic acid Following the procedure of Examples 20, 3, 34 and 37 except substituting 1-pentanethiol for 1-hexanethiol, the title compound is obtained.

EXAMPLE 69

(1β,2α,3α,4β)-7-[3-[2-(Phenylsulfinyl)ethyl]-7-oxabicyclo[2.2.1]hept-2-yl]heptanoic acid Following the procedure of Examples 20, 3, 34 and 38 except substituting phenylmercaptan for 1-hexanethiol, the title compound is obtained.

EXAMPLE 70

(1β,2α,3α,4β)-7-[3-[2-(Benzylsulfinyl)ethyl]-7-oxabicyclo[2.2.1]hept-2-yl]heptanoic acid Following the procedure of Examples 20, 3, 34 and 38 except substituting benzylmercaptan for 1-hexanethiol, the title compound is obtained.

EXAMPLE 71

(1β,2α,3α,4β)-7-[3-[2-(Cyclohexylsulfonyl)ethyl]-7-oxabicyclo[2.2.1]hept-2-yl]heptanoic acid Following the procedure of Examples 20, 5, 34 and 37 except substituting cyclohexylmercaptan for 1-hexanethiol, the title compound is obtained.

EXAMPLE 72

[1β,2α(5Z),3α,4β]-7-[3-[4-(Pentylsulfonyl)butyl]-7-oxabicyclo[2.2.1]hept-2-yl]-5-heptenoic acid Following the procedure of Examples 30, 20, 1, 34 and 37 except substituting pentylmercaptan for 1-hexanethiol, the title compound is obtained.

EXAMPLE 73

[1β,2α(5Z),3α,4β]-7-[3-[4-(cyclohexylsulfinyl)butyl]-7-oxabicyclo[2.2.1]hept-2-yl]-5-heptenoic acid Following the procedure of Examples 30, 20, 1, 34 and 38 except substituting cyclohexylmercaptan for 1-hexanthiol, the title compound is obtained.

EXAMPLE 74

[1β,2α(5Z), 3α,4β]-7-[3-[4-(Phenylsulfinyl)butyl]-7-oxabicyclo[2.2.1]hept-2-yl]-5-heptenoic acid Following the procedure of Examples 30, 20, 1, 34 and 38 except substituting phenylmercaptan for 1-hexanethiol, the title compound is obtained.

EXAMPLE 75

[1,β,2α(5Z),3α,4β]-7-[3-[4-(Benzylsulfonyl)butyl]-7-oxabicyclo[2.2.1]hept-2-yl]-5-heptenoic acid Following the procedure of Examples 30, 20, 1, 34 and 37 except substituting benzylmercaptan for 1-hexanethiol, the title compound is obtained.

EXAMPLE 76

[1β,2α(5Z),3β,4β]-7-[3-[4-(Cyclopentylsulfinyl)butyl]-7-oxabicyclo[2.2.1]hept-2-yl]-5-heptenoic acid Following the procedure of Examples 30, 20, 5, 34 and 38 except substituting cyclopentylmercaptan for 1-pentanethiol, the title compound is obtained.

EXAMPLE 77

[1β,2α(5Z),3β,4β]-7-[3-[4-(Benzylsulfinyl)butyl]-7-oxabicyclo[2.2.1]hept-2-yl]-5-heptenoic acid Following the procedure of Examples 30, 20, 5, 34 and 37 except substituting benzylmercaptan for 1-pentanethiol, the title compound is obtained.

EXAMPLE 78

[1β,2α(5Z), 3β,4β]-7-[3-[4-(Propylsulfinyl)butyl]-7-oxabicyclo[2.2.1]hept-2-yl]-5-heptenoic acid Following the procedure of Examples 30, 20, 5, 34 and 38 except substituting propylmercaptan for 1-pentanethiol, the title compound is obtained.

EXAMPLE 79

[1β,2α(5Z),3β,4β]-7-[3-[4-(Phenylsulfonyl)butyl]-7-oxabicyclo[2.2.1]hept-2-yl]-5-heptenoic acid Following the procedure of Examples 30, 20, 5, 35 and 37 except substituting phenylmercaptan for 1-pentanethiol, the title compound is obtained.

EXAMPLE 80

(1β,2α3α,4β)-7-[3-[4-(Nonylsulfinyl)butyl]-7-oxabicyclo[2.2.1]hept-2-yl]heptanoic acid Following the procedure of Examples 30, 20, 3, 34 and 38 except substituting 1-nonanethiol for 1-hexanethiol, the title compound is obtained.

EXAMPLE 81

(1β,2α,3α,4β)-7-[3-[4-(Pentylsulfonyl)butyl]-7-oxabicyclo[2.2.1]hept-2-yl]heptanoic acid Following the procedure of Examples 30, 20, 3, 34 and 37 except substituting 1-pentanethiol for 1-hexanethiol, the title compound is obtained.

EXAMPLE 82

(1β,2α,3α,4β)-7-[3-[4-(Phenylsulfinyl)butyl]-7-oxabicyclo[2.2.1]hept-2-yl]heptanoic acid Following the procedure of Examples 30, 20, 3, 34 and 38 except substituting phenylmercaptan for 1-hexanthiol, the title compound is obtained.

EXAMPLE 83

(1β,2α,3α,4β)-7-[3-[4-(Cyclohexylsulfonyl)butyl]-7-oxabicyclo[2.2.1]hept-2-yl]heptanoic acid Following the procedure of Examples 30, 20, 3, 34 and 37 except substituting cyclohexylmercaptan for 1-hexanethiol, the title compound is obtained.

EXAMPLE 84

[1β,2α(5Z), 3α,4β]-7-[3-[[(Cyclohexylmethyl)thio]-methyl]-7-oxabicyclo[2.2.1]hept-2-yl]-5-heptenoic acid

A.

[1β,2α(5Z),3α,4β]-7-[3-[[(Cyclohexylmethyl)thio]methyl]-7-oxabicyclo [2.2.1]-hept-2-yl]-5-heptenoic acid, methyl ester To a solution of 88 mg (0.78 mmol) of potassium t-butoxide in 5 ml of dry THF under argon was added 277 mg (2.13 mmol) of cyclohexylmethanethiol (prepared from cyclohexylmethanol by the method of Volante: Tetrahedron Letters 1981, 22, 3119). To this mixture was added a solution of 300 mg (0.71 mmol) of [1β,2α(5Z),3α,4β,]-7-[3-(p-toluenesulfonyloxymethyl)-7-oxabicyclo[2.2.1]-hept-2-yl]-5-heptenoic acid, methyl ester, prepared as described in Example 1B, in 5.5 ml of dry THF. The reaction mixture was heated to reflux for 7 hours. The cooled reaction mixture was diluted with 250 ml of ether and poured into 100 ml of saturated NaHCO$_3$ solution. The aqueous layer was extracted with ether (2×100 ml). The combined ether extracts (450 ml) were washed with 0.5N aqueous sodium hydroxide solution (2×φml) and brine (100 ml). The ether extracts were dried over anhydrous MgSO$_4$ and concentrated in vacuo to give an oily product. Purification was effected by chromatography on 20.2 g of silica gel 60 using hexane:ether (3:1) as eluant to give 253 mg of title A methyl ester as an oil (94%). TLC:silica gel, petroleum ether:ether (3:2), R$_f$=0.70, iodine.

B.

[1β,2α(5Z),3α,4β]-7-[3-[[(Cyclohexylmethyl)thio]methyl]-7-oxabicyclo]2.2.1]-hept-2-yl]-5-heptenoic acid To a stirred solution of 243 mg (0.64 mmol) of Part A methyl ester in 31.4 ml of THF and 4.80 ml of H$_2$O under argon was added 6.00 ml of 1N aqueous lithium hydroxide solution. This mixture was purged with argon vigorously for 25 minutes and stirred at room temperature for 16 hours. The reaction mixture was acidified to pH 5 by addition of 1N aqueous HCl solution and poured into 40 ml of saturated NaCl solution. The resulting solution was saturated with solid NaCl and extracted with EtOAc (4×50 ml). The combined EtOAc extracts were dried (MgSO$_4$), filtered and concentrated in vacuo to give 253 mg of crude acid. Purification was effected by flash chromatography on 20.6 g of silica gel 60 using petroleum-ether:ether (2:3) as eluant to give pure title product (117 mg, 50%) along with 108 mg (46%) of mixed fractions of which title product was the major component. TLC:silica gel, Pet-ether:ether (2:3), R$_f$=0.32, iodine.

Anal. Calcd for C$_{21}$H$_{34}$O$_3$S: C, 68.85; H, 9.29; S, 8.74 Found: C, 68.90; H, 9.43; S, 8.66

EXAMPLE 85

[1β,2α(5Z),3α,4β]-7-[3-[[(2-Phenylethyl)thio]methyl]-7-oxabicyclo[2.2.1]hept-2-yl]-5-heptenoic acid

A.

[1β,2α(5Z),3α,4β]-7-[3-[[(2-Phenylethyl)-thio]methyl]-7-oxabicyclo[2.2.1]hept-2-yl]-5-heptenoic acid, methyl ester To a solution of 55.7 mg (0.50 mmol) of potassium t-butoxide in 5 ml of dry THF under argon was added 185 mg (1.35 mmol) of phenylethanethiol. To this mixture was added a solution of 189 mg (0.45 mmol) of [1β,2α(5Z),3α,4β,]-7-[3-(p-toluenesulfonyloxymethyl)-7-oxabicyclo[2.2.1]hept-2-yl]-5-heptenoic acid, methyl ester, prepared as described in Example 1B, in 6 ml of dry THF. The reaction mixture was heated to reflux for 4 hours and 30 minutes. The cooled reaction mixture was diluted with 160 ml of ether and poured into 60 ml of saturated NaHCO$_3$ solution. The aqueous layer was extracted with ether (2×60 ml). The combined ether extracts (280 ml) were washed with 0.5N aqueous sodium hydroxide solution (2×60 ml) and brine (75 ml). The ether extracts were dried over MgSO$_4$ and concentrated in vacuo to give an oily product. Purification was effected by chromatography on 21.6 g of silic gel 60 using petroleum ether:ether (5:1) as eluant to give 157 mg of title A compound as an oil (90%). TLC:silica gel, petroleum ether:ether (2:1), R$_f$=0.60, iodine.

B.

[1β,2α(5Z),3α,4β]-7-[3-[[(2-Phenylethyl)-thio]methyl]-7-oxabicyclo[2.2.1]hept-2-yl]-5-heptenoic acid To a stirred solution of 150 mg (0.39 mmol) of Part A methyl ester in 19 ml of freshly distilled THF and 2.91 ml of H$_2$O under argon was added 3.64 ml of 1N aqueous lithium hydroxide solution. This mixture was purged with argon vigorously for 25 minutes and stirred at room temperature for 6 hours. The reaction mixture was acidified to pH 5 by addition of 1N aqueous HCl solution and poured into 40 ml of saturated NaCl solution. The resulting solution was saturated with solid NaCl and extracted with EtOAc (4×60 ml). The combined EtOAc extracts were dried (MgSO$_4$), filtered and concentrated in vacuo to give 147 mg of crude acid. Purification was effected by flash chromatography on 20 g of silica gel 60 using 2% CH$_3$OH in CH$_2$Cl$_2$ as eluant to give title product (122 mg, 84%) as an oil. TLC:silica gel, 6% CH$_3$OH in CH$_2$Cl$_2$, R$_f$=0.32, iodine.

Anal. Calcd for C$_{22}$H$_{30}$O$_3$S: C, 70.55; H, 8.07; S, 8.56 Found: C, 70.54; H, 8.08; S, 8.48

EXAMPLE 86

[1β,2α(5Z),3α,4β]-7-[3-[[(3-Phenylpropyl)thio]methyl]-7-oxabicyclo[2.2.1]hept-2-yl]-5-heptenoic acid

A.

[1β,2α(5Z),3α,4β]-7-[3-[[(3-Phenylpropyl)-thio]methyl]-7-oxabicyclo[2.2.1]hept-2-yl]-5-heptenoic acid, methyl ester To a solution of 88 mg (0.78 mmol) of potassium t-butoxide in 5 ml of dry THF under argon was added 324 mg (2.13 mmol) of 3-phenylpropylmercaptan. To this mixture was added a solution of 300 mg (0.71 mmol) of [1β,2α(5Z),3α,4β]-7-[3-(p-toluenesulfonyloxymethyl)-7-oxabicyclo[2.2.1]-hept-2-yl]-5-heptenoic acid, methyl ester in 7 ml of dry THF. The reaction mixture was heated to reflux for 6 hours and 30 minutes. The cooled reaction mixture was diluted with 250 ml of ether and poured into 100 ml of saturated NaHCO$_3$ solution. The aqueous layer was extracted with ether (2×100 ml). The combined ether extracts (450 ml) was washed with 0.5N aqueous sodium hydroxide solution (2×100 ml) and brine (100 ml). The ether extracts were dried over MgSO$_4$ and concentrated in vacuo to give an oily product. Purification was effected by chromatography on 25 g of silica gel 60 using hexane:ether (3:1) as eluant to give 280 mg of title A compound as an oil (98%). TLC:silica gel, petroleum ether:ether (2:1), R$_f$ 0.60, iodine.

B.

[1β,2α(5Z),3α,4β]-7-[3-[[(3-Phenylpropyl)-thio]methyl]-7-oxabicyclo[2.2.1]hept-2-yl]-5-heptenoic acid To a stirred solution of 280 mg (0.70 mmol) of Part A methyl ester in 34.4 ml of freshly distilled THF and 5.30 ml of H$_2$O under argon was added 6.60 ml of 1N aqueous lithium hydroxide solution. This mixture was purged with argon for an hour and stirred at room temperature for 3 hours. The reaction mixture was acidified to pH 5 by addition of 1N aqueous HCl solution and poured into 50 ml of saturated NaCl solution. The resulting solution was saturated with solid NaCl and extracted with EtOAc (4×60 ml). The combined EtOAc extracts were dried (MgSO$_4$), filtered and concentrated in vacuo to give 280 mg of crude acid. Purification was effected by flash chromatography on 29 g of silica gel 60 using 2% CH$_3$OH in CH$_2$Cl$_2$ eluant to give title product (205 mg, 76%). TLC:silica gel, 6% CH$_3$OH/CH$_2$Cl$_2$, R$_f$=0.34, iodine.

Anal. Calcd for C$_{23}$H$_{32}$O$_3$S: C, 71.09; H, 8.30; S, 8.25 Found: C 70.81; H, 8.36; S, 8.14

EXAMPLE 87

[1β,2α(5Z),3β,4β]-7-[3-[[(Cyclohexylmethyl)-thio]methyl]-7-oxabicyclo[2.2.1]hept-2-yl]-5-heptenoic acid Following the procedure of Examples 5 and 6 except substituting cyclohexylmethanethiol for 1-pentanethiol, the title compound is obtained.

EXAMPLE 88

[1β,2α(5Z),3β,4β]-7-[3-[[(3-Cyclohexylpropyl)thio]methyl]-7-oxabicyclo[2.2.1]hept-2-yl]-5-heptenoic acid Following the procedure of Examples 5 and 6 except substituting 3-cyclohexylpropanethiol for 1-pentanethiol, the title compound is obtained.

EXAMPLE 89

(1β,2α,3α,4β)-7-[3-[[(2-Cyclohexylethyl)thio]methyl]-7-oxabicyclo[2.2.1]hept-2yl heptanoic acid Following the procedure of Examples 3 and 4 except substituting 2-cyclohexylethanethiol for 1-hexanethiol, the title compound is obtained.

EXAMPLE 90

[1β,2α(5Z),3β,4β]-7-[3-[[(2-Phenylethyl)thio]methyl]-7-oxabicyclo[2.2.1]hept-2-yl]-5-heptenoic acid Following the procedure of Examples 5 and 6 except substituting 2-phenylethanethiol for 1-pentanethiol, the title compound is obtained.

EXAMPLE 91

[1β,2α(5Z),3β,4β]-7-[3-[[(3-Phenylpropyl)thio]methyl]-7-oxabicyclo[2.2.1]hept-2-yl]-5-heptenoic acid Following the procedure of Examples 5 and 6 except substituting 3-phenylpropanethiol for 1-pentanethiol, the title compound is obtained.

EXAMPLE 92

(1β,2α,3α,4β)-7-[3-[[(2-Phenylethyl)thio]methyl]-7-oxabicyclo[2.2.1]hept-2 -yl]heptanoic acid Following the procedure of Examples 3 and 4 except substituting 2-phenylethanethiol for 1-hexanethiol, the title compound is obtained.

EXAMPLE 93

(1β,2α,3α,4β)-7-[3-[[(3-Phenylpropyl)thio]methyl]-7-oxabicyclo[2.2.1]hept-2-yl]heptanoic acid Following the procedure of Examples 3 and 4 except substituting 3-phenylpropanethiol for 1-hexanethiol, the title compound is obtained.

EXAMPLE 94

[1β,2α(5Z),3α,4β]-7-[3-[[(Cyclohexylmethyl)sulfinyl]-methyl]-7-oxabicyclo[2.2.1]hept -2yl] -5-heptenoic acid (slow moving isomer)

Following the procedure of Examples 1, 34, and 39 except substituting cyclohexylmethanethiol for 1-hexanethiol, the title compound is obtained.

EXAMPLE 95

[1β,2α(5Z),3β,4β]-7-[3-[[(Cyclohexylmethyl)sulfinyl]-methyl]-7-oxabicyclo[2.2.1]hept-2-yl]-5-heptenoic acid (fast moving isomer)

Following the procedure of Examples 5, 34 and 38 except substituting cyclohexylmethanethiol for 1-pentanethiol, the title compound is obtained.

EXAMPLE 96

[1β,2α(5Z), 3β,4β]-7-[3-[[(2-Phenylethyl)sulfinyl]-methyl]-7-oxabicyclo[2.2.1]hept-2-yl]-5-heptenoic acid (fat moving isomer)

Following the procedure of Examples 5, 34 and 38 except substituting 2-phenylethanethiol for 1-pentanethiol, the title compound is obtained.

EXAMPLE 97

[1β2α(5Z),3α,4β]-7-[3-[[(3-Phenylpropyl)sulfinyl]-methyl]-7-oxabicyclo[2.2.1]hept-2yl]-5-heptenoic acid (slow moving isomer)

Following the procedure of Examples 5, 34 and 39 except substituting 3-phenylpropanethiol for 1-pentanethiol, the title compound is obtained.

EXAMPLE 98

(1β,2α,3α,4β)-7-[3-[[(2-Phenylethyl)sulfinyl]methyl]-7-oxabicyclo[2.2.1]hept-2-yl]heptanoic acid (fast moving isomer)

Following the procedure of Examples 3, 34 and 38 except substituting 2-phenylethanethiol for 1hexanethiol, the title compound is obtained.

EXAMPLE 99

[1β,2α(5Z),3α,4β]-7-[3-[[(Cyclohexylmethyl)sulfonyl]methyl]-7-oxabicyclo[2.2.1]hept-2-yl]-5-heptenoic acid Following the procedure of Examples 1, 34 and 37 except substituting cyclohexylmethanethiol for 1-hexanethiol, the title compound is obtained.

EXAMPLE 100

[1β,2α(5Z),3α,4β]-7-[3-[[(2-Phenylethyl)sulfonyl]methyl]-7-oxabicyclo[2.2.1]hept-2-yl]-5-heptenoic acid Following the procedure of Examples 1, 34 and 37 except substituting 2-phenylethanethiol for 1-hexanethiol, the title compound is obtained.

EXAMPLE 101

[1β,2α(5Z),3α,4β]-7-[3-[[(3-Phenylpropyl)sulfonyl]methyl]-7-oxabicyclo[2.2.1]hept-2-yl]-5-heptenoic acid Following the procedure of Examples 1, 34 and 37 except substituting 3-phenylpropanethiol for 1-hexanethiol, the title compound is obtained.

EXAMPLE 102

[1β,2α(5Z),3α,4β]-7-[3-[2-[(Cyclohexylmethyl)thio]ethyl]-7-oxabicyclo[2.2.1]hept-2-yl]-5-heptenoic acid Following the procedure of Examples 20 and 1 except substituting cyclohexylmethanethiol for 1-hexanethiol, the title compound is obtained.

EXAMPLE 103

[1β,2α(5Z),3α,4β]-7-[3-[2-[(Cyclohexylmethyl)sulfinyl]-ethyl]-7-oxabicyclo[2.2.1]hept-2-yl]-5-heptenoic acid Following the procedure of Examples 20, 1, 34 and 38 except substituting cyclohexylmethanethiol for 1-hexanethiol, the title compound is obtained.

EXAMPLE 104

[1β,2α(5Z),3α,4β]-7-[3-[2-[(Cyclohexylmethyl)-sulfonyl]ethyl]-7-oxabicyclo[2.2.1]hept-2yl]-5-heptenoic acid Following the procedure of Examples 20, 1, 34 and 37 except substituting cyclohexylmethanethiol for 1-hexanethiol, the title compound is obtained.

EXAMPLE 105

[1β,2α(5Z),3α,4β]-7-[3-[2-[(2-Phenylethyl)thio]-ethyl]-7-oxabicyclo[2.2.1]hept-2-yl]-5-heptenoic acid Following the procedure of Examples 20 and 1 except substituting 2-phenylethanethiol for 1-hexanethiol, the title compound is obtained.

EXAMPLE 106

[1β,2α(5Z),3β,4β]-7-[3-[2-[(2-Phenylethyl)sulfinyl]-ethyl]-7-oxabicyclo[2.2.1]hept-2-yl]-5-heptenoic acid Following the procedure of Examples 20, 1, 34 and 38 except substituting 2-phenylethanethiol for 1-hexanethiol, the title compound is obtained.

EXAMPLE 107

[1β,2α(5Z),3α,4β]-7-[2-[(3-Phenylpropyl)thio]ethyl]-7-oxabicyclo[2.2.1]hept-2-yl]-5-heptenoic acid Following the procedure of Examples 20 and 1 except substituting 3-phenylpropanethiol for 1-hexanethiol, the title compound is obtained.

EXAMPLE 108

[1β,2α(5Z),3α,4β]-7-[3-[2-[(3-Phenylpropyl)sulfinyl]-ethyl]-7-oxabicyclo[2.2.1]hept-2-yl]-5-heptenoic acid Following the procedure of Examples 20, 1, 34 and 38 except substituting 3-phenylpropanethiol for 1-hexanethiol, the title compound is obtained.

EXAMPLE 109

[1β,2α(5Z),3α,4β]-7-[3-[2-[(2-Phenylethyl)sulfonyl]-ethyl]-7-oxabicyclo[2.2.1]hept-2-yl]-5-heptenoic acid Following the procedure of Examples 20, 1, 34 and 37 except substituting 2-phenylethanethiol for 1-hexanethiol, the title compound is obtained.

EXAMPLE 110

[1β,2α(5Z),3α,4β]-7-[3-[2-[(3-Phenylpropyl)sulfonyl]-ethyl]-7-oxabicyclo[2.2.1]hept-2yl]-5-heptenoic acid Following the procedure of Examples 20, 1, 34 and 37 except substituting 3-phenylpropanethiol for 1-hexanethiol, the title compound is obtained.

EXAMPLE 111

[1β,2α(5Z),3α,4β]-7-[3-[4-[(Cyclohexylmethyl)thio]-butyl]-7-oxabicyclo[2.2.1]hept-2-yl]-5-heptenoic acid Following the procedure of Examples 30, 20 and 1 except substituting cyclohexylmethanethiol for 1-hexanethiol, the title compound is obtained.

EXAMPLE 112

[1β,2α(5Z),3α,4β]-7-[3-[4-[(Cyclohexylmethyl)-sulfinyl]butyl]-7-oxabicyclo[2.2.1]hept-2-yl]-5-heptenoic acid Following the procedure of Examples 30, 20 1, 34 and 38 except substituting cyclohexylmethanethiol for 1-hexanethiol, the title compound is obtained.

EXAMPLE 113

[1β,2α(5Z),3α,4β]-7-[3-[4-[(Cyclohexylmethyl)-sulfonyl]butyl]-7-oxabicyclo[2.2.1]hept-2-yl]-5-heptenoic acid Following the procedure of Examples 30, 20, 1, 34 and 37 except substituting cyclohexylmethanethiol for 1-hexanethiol, the title compound is obtained.

EXAMPLE 114

[1β,2α(5Z),3α,4β]-7-[3-[4-[(2-Phenylethyl)thio]-butyl]-7-oxabicyclo[2.2.1]hept-2-yl]-5-heptenoic acid Following the procedure of Examples 30, 20, and 1 except substituting 2-phenylethanethiol for 1-hexanethiol, the title compound is obtained.

EXAMPLE 115

[1β,2α(5Z),3α,4β]-7-[3-[4-[(2-Phenylethyl)sulfinyl]-butyl]-7-oxabicyclo[2.2.1]hept-2-yl]-5-heptenoic acid Following the procedure of Examples 30, 20, 1, 34 and 38 except substituting 2-phenylethanethiol for 1-hexanethiol, the title compound is obtained.

EXAMPLE 116

[1β,2α(5Z),3α,4β]-7-[3-[4-[(2-Phenylethyl)sulfonyl]-butyl]-7-oxabicyclo[2.2.1]hept-2-yl]-5-heptenoic acid Following the procedure of Examples 30, 20, 1, 34 and 37 except substituting 2-phenylethanethiol for 1-hexanethiol, the title compound is obtained.

What is claimed is:

1. A compound having the structural formula

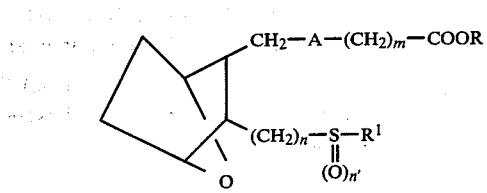

and including all stereoisomers thereof, wherein A is —CH=CH— or —(CH$_2$)$_2$—;

m is 1 to 8; n is 1 to 4; n' is 0, 1 or 2;

R is hydrogen, lower alkyl or alkali metal; and R$^1$ is lower alkyl, aryl, aralkyl, cycloalkyl or cycloalkylalkyl, wherein alkyl by itself or as part of another group contains 1 to 12 carbon atoms and may be unsubstituted or substituted with a halogen, an alkoxy group, a haloaryl group, a cycloalkyl group or an alkylcycloalkyl group; cycloalkyl by itself or as part of another group contains 3 to 12 carbon atoms in the ring portion and may be unsubstituted or substituted with 1 to 2 halogens, 1 or 2 lower alkyl groups and/or lower alkoxy groups; aryl by itself or as part of another group represents monocyclic or bicyclic aromatic groups which contain 6 to 10 carbon atoms which may be unsubstituted or substituted with a lower alkyl group, a halogen or a lower alkoxy group.

2. The compound as defined in claim 1 wherein A is —CH=CH—.

3. The compound as defined in claim 1 wherein R is H.

4. The compound as defined in claim 1 wherein n' is 0.

5. The compound as defined in claim 1 wherein N' is 1.

6. The compound as defined in claim 1 wherein n' is 2.

7. The compound as defined in claim 1 wherein A is —CH=CH—, m is 2 to 4, n is 1 or 2, n' is 0, R is H and R$^1$ is lower alkyl or cycloalkyl.

8. The compound as defined in claim 1 wherein A is —CH=CH—, m is 3, n is 1, n' is 0, R is H or CH$_3$, and R$^1$ is lower alkyl.

9. The compound as defined in claim 1 wherein A is —CH=CH—, m is 3, n is 1, n' is 1 and R$^1$ is lower alkyl.

10. The compound as defined in claim 1 wherein A is —CH=CH—, m is 3, n is 1, n' is 2 and R' is lower alkyl.

11. The compound as defined in claim 1 having the name [1β,2α(5Z), 3α,4β]-7-[3-[(hexylthio)-methyl]-7-oxabicyclo [2.2.1]hept-2-yl]-5-heptenoic acid or its methyl ester.

12. The compound as defined in claim 1 having the name [1β,2α(5Z),3α,4β]-7-[3-[(hexylsulfinyl)methyl]-7-oxabicyclo[2.2.1]hept-2-yl]-5-heptenoic acid or its methyl ester.

13. The compound as defined in claim 1 having the name [1β,2α,(5Z),3α,4β]-7-[3-[(hexylsulfonyl)-methyl]-7-oxabicyclo[2.2.1]hept-2-yl]-7-heptenoic acid or the methyl ester thereof.

14. The compound as defined in claim 1 having the name [1β,2α(5Z),3α,4β]-7-[3-[[(Cyclohexylmethyl)thio]methyl]-7-oxabicyclo[2.2.1]hept-2-yl]-5-heptenoic acid or the methyl ester thereof.

15. The compound as defined in claim 1 having the name [1β,2α(5Z),3α,4β]-7-[3-[[(2-phenylethyl)thio]methyl]-7-oxabicyclo[2.2.1]hept-2-yl]-5-heptenoic acid or the methyl ester thereof.

16. The compound as defined in claim 1 having the name [1β,2α(5Z),3α,4β]-7-[3-[[(3-phenylpropyl)thio]-methyl]-7-oxabicyclo[2.2.1]hept-2-yl]-5-heptenoic acid or the methyl ester thereof.

17. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

18. The method as defined in claim 17 wherein said compound is administered in an amount with the range of from about 1 to about 100 mg/kg.

19. A composition for inhibiting archidonic acid-induced platelet aggregation and bronchoconstriction comprising an effective amount of a compound as defined in claim 1 or a pharmaceutically acceptable salt thereof, and a pharmaceutically acceptable carrier therefor.

20. A method of inhibiting platelet aggregation which comprises administering to a mammalian host an effective amount of a compound as defined in claim 1 or a pharmaceutically acceptable salt thereof.

21. A method of inhibiting bronchoconstriction associated with asthma, which comprises administering to a mammalian host an effective amount of a compound as defined in claim 1 or a pharmaceutically acceptable salt thereof.

22. A method for inhibiting arachidonic acid-induced platelet aggregation and bronchoconstriction by inhibiting production of thromboxane A$_2$ by blocking the action of thromboxane synthetase, which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,474,803

DATED : October 2, 1984

INVENTOR(S) : Steven E. Hall et al.

It is certified that error appears in the above—identified patent and that said Letters Patent is hereby corrected as shown below:

Column 12, line 46, delete "-5-".
Column 12, line 52 should read --[1β,2α(5Z),3β,4β]-7-
   [3-[(Pentylthio)methyl]-7- --.
Column 12, line 68, after "100 ml)" insert --, and 0.5
   N aqueous NaOH solution (3 x 100 ml)--
Column 18, line 56 should read --[1β,2α(5Z),3α,4β]-7-
   [3-[(hexylsulfonyl)methyl]-7- --.
Column 19, line 47, "hept-2-yl[" should read
   --hept-2-yl]--.
Column 24, line 55, between "2α" and "3α" insert a
   comma.
Column 25, line 41, "(2 x ∅ml)" should read
   (2 x 100 ml).
Column 28, line 62, between "1β" and "2α" insert a
   comma.
Column 31, line 63, "N' " should read --n'--.

Signed and Sealed this

Fourteenth Day of May 1985

[SEAL]

Attest:

DONALD J. QUIGG

Attesting Officer         Acting Commissioner of Patents and Trademarks

UNITED STATES PATENT AND TRADEMARK OFFICE
CERTIFICATE OF CORRECTION

PATENT NO. : 4,474,803

DATED : October 2, 1984

INVENTOR(S) : Steven E. Hall et al.

It is certified that error appears in the above—identified patent and that said Letters Patent is hereby corrected as shown below:

Column 2, line 35, "n" should read --n'--.

Signed and Sealed this

Twenty-fourth Day of June 1986

[SEAL]

Attest:

Attesting Officer

DONALD J. QUIGG

Commissioner of Patents and Trademarks